(12) United States Patent
Hettrick et al.

(10) Patent No.: US 11,304,749 B2
(45) Date of Patent: Apr. 19, 2022

(54) SYSTEMS, DEVICES, AND ASSOCIATED METHODS FOR NEUROMODULATION WITH ENHANCED NERVE TARGETING

(71) Applicant: Medtronic Ardian Luxembourg S.a.r.l., Luxembourg (LU)

(72) Inventors: Douglas A. Hettrick, Andover, MN (US); Julie Trudel, Santa Rosa, CA (US); Paul Coates, Santa Rosa, CA (US); Robert J. Melder, Santa Rosa, CA (US); Stefan S. Tunev, Santa Rosa, CA (US); Martin Rothman, Santa Rosa, CA (US); Sean Salmon, Santa Rosa, CA (US)

(73) Assignee: MEDTRONIC ARDIAN LUXEMBOURG S.A.R.L., Luxembourg (LU)

( * ) Notice: Subject to any disclaimer, the term of this patent is extended or adjusted under 35 U.S.C. 154(b) by 473 days.

(21) Appl. No.: 16/191,000

(22) Filed: Nov. 14, 2018

(65) Prior Publication Data

US 2019/0151013 A1    May 23, 2019

Related U.S. Application Data

(60) Provisional application No. 62/588,215, filed on Nov. 17, 2017.

(51) Int. Cl.
*A61B 18/14* (2006.01)
*A61B 5/00* (2006.01)
(Continued)

(52) U.S. Cl.
CPC ........ *A61B 18/1492* (2013.01); *A61B 5/0538* (2013.01); *A61B 5/4836* (2013.01);
(Continued)

(58) Field of Classification Search
CPC . A61B 18/1492; A61B 5/4836; A61B 5/0538; A61B 2018/00666; A61B 5/0035;
(Continued)

(56) References Cited

U.S. PATENT DOCUMENTS 4,602,624 A    7/1986   Naples et al.
4,649,936 A    3/1987   Ungar et al.
(Continued)

FOREIGN PATENT DOCUMENTS

EP    2457615    12/2014
EP    2934357    11/2017
(Continued)

OTHER PUBLICATIONS

Brown, "Electrical impedance tomography (EIT): a review," Journal of Medical Engineering and Technology, vol. 27, No. 3, May/Jun. 2003, pp. 107-108.
(Continued)

*Primary Examiner* — Linda C Dvorak
*Assistant Examiner* — Lindsay Regan Lancaster
(74) *Attorney, Agent, or Firm* — Shumaker & Sieffert, P.A.

(57) ABSTRACT

Systems and methods for neuromodulation therapy are disclosed herein. A method in accordance with embodiments of the present technology can include, for example, positioning a plurality of reference electrodes at the skin of a human patient and intravascularly positioning a plurality of ablation electrodes within a blood vessel lumen at a treatment site. The method can include obtaining impedance measurements between different combinations of the reference electrodes and the ablation electrodes and, based on the impedance measurements, identifying two or more electrode groups for
(Continued)

treatment, where at least two of the electrode groups include a different one of the reference electrodes and a different one of the ablation electrodes.

23 Claims, 11 Drawing Sheets

(51) Int. Cl.
    *A61B 5/0538*    (2021.01)
    *A61B 18/12*    (2006.01)
    *A61B 18/16*    (2006.01)
    *A61B 18/00*    (2006.01)
    *A61B 5/0531*    (2021.01)

(52) U.S. Cl.
    CPC ........... *A61B 5/0035* (2013.01); *A61B 5/0036* (2018.08); *A61B 5/0531* (2013.01); *A61B 2018/00404* (2013.01); *A61B 2018/00434* (2013.01); *A61B 2018/00577* (2013.01); *A61B 2018/00636* (2013.01); *A61B 2018/00642* (2013.01); *A61B 2018/00648* (2013.01); *A61B 2018/00654* (2013.01); *A61B 2018/00666* (2013.01); *A61B 2018/00702* (2013.01); *A61B 2018/00755* (2013.01); *A61B 2018/00875* (2013.01); *A61B 2018/124* (2013.01); *A61B 2018/1467* (2013.01); *A61B 2018/165* (2013.01); *A61B 2018/167* (2013.01)

(58) Field of Classification Search
    CPC ........... A61B 2018/00654; A61B 2018/00755; A61B 5/0036; A61B 2018/00636; A61B 5/0531; A61B 2018/1467; A61B 2018/124; A61B 2018/167; A61B 2018/165; A61B 2018/00434; A61B 2018/00577; A61B 2018/00642; A61B 2018/00702; A61B 2018/00875
    See application file for complete search history.

(56) References Cited

U.S. PATENT DOCUMENTS

| | | | |
|---|---|---|---|
| 4,764,504 A | 8/1988 | Johnson et al. | |
| 4,976,711 A | 12/1990 | Parins et al. | |
| 5,300,068 A | 4/1994 | Rosar et al. | |
| 5,358,514 A | 10/1994 | Schulman et al. | |
| 5,423,744 A | 6/1995 | Gencheff et al. | |
| 5,571,147 A | 11/1996 | Sluijter et al. | |
| 5,626,576 A | 5/1997 | Janssen | |
| 5,700,282 A | 12/1997 | Zabara | |
| 5,707,400 A | 1/1998 | Terry, Jr. et al. | |
| 5,865,787 A | 2/1999 | Shapland | |
| 5,944,710 A | 8/1999 | Dev et al. | |
| 5,983,141 A | 11/1999 | Sluijter et al. | |
| 6,004,269 A | 12/1999 | Crowley et al. | |
| 6,009,877 A | 1/2000 | Edwards | |
| 6,066,134 A | 5/2000 | Eggers et al. | |
| 6,099,524 A | 8/2000 | Lipson et al. | |
| 6,117,101 A | 9/2000 | Diederich et al. | |
| 6,149,620 A | 11/2000 | Baker et al. | |
| 6,161,048 A | 12/2000 | Sluijter et al. | |
| 6,219,577 B1 | 4/2001 | Brown, III et al. | |
| 6,224,592 B1 | 5/2001 | Eggers et al. | |
| 6,246,912 B1 | 6/2001 | Sluijter et al. | |
| 6,273,886 B1 | 8/2001 | Edwards et al. | |
| 6,283,951 B1 | 9/2001 | Flaherty et al. | |
| 6,292,695 B1 | 9/2001 | Webster, Jr. et al. | |
| 6,405,732 B1 | 6/2002 | Edwards et al. | |
| 6,506,189 B1 | 1/2003 | Rittman et al. | |
| 6,514,226 B1 | 2/2003 | Levin et al. | |
| 6,522,926 B1 | 2/2003 | Kieval et al. | |
| 6,562,034 B2 | 5/2003 | Edwards et al. | |
| 6,635,054 B2 | 10/2003 | Fjield et al. | |
| 6,685,648 B2 | 2/2004 | Flaherty et al. | |
| 6,736,835 B2 | 5/2004 | Pellegrino et al. | |
| 6,845,267 B2 | 1/2005 | Harrison et al. | |
| 6,850,801 B2 | 2/2005 | Kieval et al. | |
| 6,885,888 B2 | 4/2005 | Rezai | |
| 6,893,436 B2 | 5/2005 | Woodard et al. | |
| 7,149,574 B2 | 12/2006 | Yun et al. | |
| 7,162,303 B2 | 1/2007 | Levin et al. | |
| 7,221,979 B2 | 5/2007 | Zhou et al. | |
| 7,381,200 B2 | 6/2008 | Katoh et al. | |
| 7,390,894 B2 | 6/2008 | Weinshilboum et al. | |
| 7,617,005 B2 | 11/2009 | Demarais et al. | |
| 7,647,115 B2 | 1/2010 | Levin et al. | |
| 7,653,438 B2 | 1/2010 | Deem et al. | |
| 7,717,948 B2 | 5/2010 | Demarais et al. | |
| 7,778,703 B2 | 8/2010 | Gross et al. | |
| 8,131,372 B2 | 3/2012 | Levin et al. | |
| 8,140,170 B2 | 3/2012 | Rezai et al. | |
| 8,145,317 B2 | 3/2012 | Demarais et al. | |
| 8,150,518 B2 | 4/2012 | Levin et al. | |
| 8,150,520 B2 | 4/2012 | Demarais et al. | |
| 8,175,711 B2 | 5/2012 | Demarais et al. | |
| 8,347,891 B2 | 1/2013 | Demarais et al. | |
| 8,888,773 B2 | 11/2014 | Chang et al. | |
| 9,060,755 B2 | 6/2015 | Buckley et al. | |
| 9,084,610 B2 | 7/2015 | Goshgarian et al. | |
| 9,168,094 B2 | 10/2015 | Lee et al. | |
| 2002/0077627 A1* | 6/2002 | Johnson | A61B 18/1477 606/41 |
| 2003/0045871 A1* | 3/2003 | Jain | A61B 18/1206 606/41 |
| 2003/0060858 A1 | 3/2003 | Kieval et al. | |
| 2005/0010209 A1* | 1/2005 | Lee | A61B 18/1477 606/41 |
| 2005/0228460 A1 | 10/2005 | Levin et al. | |
| 2006/0004301 A1 | 1/2006 | Kasevich | |
| 2006/0206150 A1 | 9/2006 | Demarais et al. | |
| 2006/0271111 A1 | 11/2006 | Demarais et al. | |
| 2007/0060832 A1* | 3/2007 | Levin | A61B 5/053 600/547 |
| 2007/0129720 A1 | 6/2007 | Demarais et al. | |
| 2007/0265687 A1 | 11/2007 | Deem et al. | |
| 2008/0319513 A1 | 12/2008 | Pu et al. | |
| 2009/0036948 A1 | 2/2009 | Levin et al. | |
| 2010/0137860 A1 | 6/2010 | Demarais et al. | |
| 2010/0137952 A1 | 6/2010 | Demarais et al. | |
| 2010/0191112 A1 | 7/2010 | Demarais et al. | |
| 2010/0222851 A1 | 9/2010 | Deem et al. | |
| 2010/0222854 A1 | 9/2010 | Demarais et al. | |
| 2012/0116382 A1* | 5/2012 | Ku | A61M 25/0147 606/33 |
| 2012/0130289 A1 | 5/2012 | Demarais et al. | |
| 2012/0130345 A1 | 5/2012 | Levin et al. | |
| 2012/0150022 A1* | 6/2012 | Bar-Tal | A61B 5/063 600/424 |
| 2012/0172837 A1 | 6/2012 | Demarais et al. | |
| 2012/0173217 A1* | 7/2012 | Heimbecher | A61B 90/90 703/7 |
| 2012/0265268 A1* | 10/2012 | Blum | A61N 1/36021 607/46 |
| 2013/0096549 A1* | 4/2013 | Organ | A61B 18/1206 606/33 |
| 2014/0100562 A1* | 4/2014 | Sutermeister | A61B 18/1233 606/35 |
| 2014/0364715 A1* | 12/2014 | Hauck | A61B 5/24 600/373 |
| 2015/0320481 A1* | 11/2015 | Cosman, Jr. | A61B 18/1233 606/35 |
| 2016/0095535 A1 | 4/2016 | Hettrick et al. | |
| 2016/0331459 A1* | 11/2016 | Townley | A61N 1/403 |

FOREIGN PATENT DOCUMENTS

| | | |
|---|---|---|
| WO | WO2012061153 | 5/2012 |
| WO | WO2012061161 | 5/2012 |

(56) References Cited

FOREIGN PATENT DOCUMENTS

| | | |
|---|---|---|
| WO | WO2015113027 | 7/2015 |
| WO | WO2015143372 | 9/2015 |
| WO | WO2017012907 | 1/2017 |

OTHER PUBLICATIONS

Esler et al., "Renal Denervation: Not as Easy as it Looks," Science Translational Medicine, vol. 7, No. 285, Apr. 29, 2015, 4 pages.

Mahfoud et al., "Efficacy and Safety of Catheter-Based Radiofrequency Renal Denervation in Stented Renal Arteries," Circ Cardiovasc Interv. 2014; 7 :813-818.

Wolf et al., "Noninvasive assessment of lung volume: Respiratory inductance plethysmography and electrical impedance tomography." Crit Care Med 2005; vol. 33(3) Supplement.S163-S169.

Coulombe et al., "A Parametric Model of the Relationship Between EIT and Total Lung Volume." Physiol Meas, 2005;26(4):401-411.

Zhang et al., "EIT Images of Ventilation: What Contributes to the Resistivity Changes?" Physiol. Meas., 2005, 26(2): S81-S92.

Brown, "Electrical impedance tomography (EIT): a review," Journal of Medical Engineering & Technology. 2003; 27:97-108.

U.S. Appl. No. 62/588,215, by Hettrick et al., filed Nov. 17, 2017.

U.S. Appl. No. 15/965,687, by Coates et al., filed Apr. 27, 2018.

U.S. Appl. No. 15/965,692, by Coates et al., filed Apr. 27, 2018.

U.S. Appl. No. 15/965,675, by Coates et al., filed Apr. 27, 2018.

Mark R. de Jong et al. "Renal Nerve Stimulation—Induced Blood Pressure Changes Predict Ambulatory Blood Pressure Response After Renal Denervation" Mar. 9, 2016, Hypertension 2016; 68:707-714.

International Searching Authority, International Search Report and Written Opinion for International Application No. PCT/IB2018/001443, dated Apr. 4, 2019, 15 pages.

Allen, E.V., Sympathectomy for essential hypertension, Circulation, 1952, 6:131-140.

Bello-Reuss, E. et al., "Effects of Acute Unilateral Renal Denervation in the Rat," Journal of Clinical Investigation, vol. 56, Jul. 1975, pp. 208-217.

Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.

Bhandari, A. and Ellias, M., "Loin Pain Hematuria Syndrome: Pain Control with RFA to the Splanchanic Plexus," The Pain Cline, 2000, vol. 12, No. 4, pp. 323-327.

Curtis, John J. et al., "Surgical Therapy for Persistent Hypertension After Renal Transplantation" Transplantation, 31:125-128 (1981).

Dibona, Gerald F. et al., "Neural Control of Renal Function," Physiological Reviews, vol. 77, No. 1, Jan. 1997, The American Physiological Society 1997, pp. 75-197.

Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.

Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.

Katholi, Richard E., "Renal Nerves in the Pathogenesis of Hypertension in Experimental Animals and Humans," Am J. Physiol. Vol. 245, 1983, the American Physiological Society 1983, pp. F1-F14.

Krum, Henry et al., "Catheter-Based Renal Sympathetic Denervation for Resistant Hypertension: A Mulitcentre Safety and Proof-of Principle Cohort Study," Lancet 2009; 373:1275-81.

Krum, et al., "Renal Sympathetic-Nerve Ablation for Uncontrolled Hypertension." New England Journal of Med, Aug. 2009, 361; 9, 3 pages.

Luippold, Gerd et al., "Chronic Renal Denervation Prevents Glomerular Hyperfiltration in Diabetic Rats", Nephrol Dial Transplant, vol. 19, No. 2, 2004, pp. 342-347.

Mahfoud et al. "Treatment strategies for resistant arterial hypertension" Dtsch Arztebl Int. 2011;108:725-731.

Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.

Page, I.H et al., "The Effect of Renal Denervation on Patients Suffering From Nephritis," Feb. 27, 1935;443-458.

Page, I.H et al., "The Effect of Renal Denervation on the Level of Arterial Blood Pressure and Renal Function in Essential Hypertension," J. Clin Invest. 1934;14:27-30.

Rocha-Singh, "Catheter-Based Sympathetic Renal Denervation," Endovascular Today, Aug. 2009, 4 pages.

Schlaich, M.P. et al., "Renal Denervation as a Therapeutic Approach for Hypertension: Novel Implications for an Old Concept," Hypertension, 2009; 54:1195-1201.

Schlaich, M.P. et al., "Renal Sympathetic-Nerve Ablation for Uncontrolled Hypertension," N Engl J Med 2009; 361(9): 932-934.

Smithwick, R.H. et al., "Splanchnicectomy for Essential Hypertension," Journal Am Med Assn, 1953; 152:1501-1504.

Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.

Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.

United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.

Valente, John F. et al., "Laparoscopic Renal Denervation for Intractable ADPKD-Related Pain", Nephrol Dial Transplant (2001) 16: 1 page.

Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.

* cited by examiner

| Tissue | Mean Resistivity with lower/upper bounds (Ohm cm) | Mean Conducitivity (S/cm) |
|---|---|---|
| Air Internal | 50,000 (50,000 to 100,000) | 2E-5 |
| Air External | 100,000 | 1E-6 |
| Basal Ganglia | 700 | 1.42E-3 |
| Blood | 160 (80 to 240) | 6.25E-3 |
| Brain White Matter | 700 (350 to 1,050) | 1.42E-3 |
| Brain Gray Matter | 300 (150 to 450) | 3.334E-3 |
| Cerebellum | 650 (325 to 975) | 1.54E-3 |
| Cerebrospinal Fluid | 65 (32.5 to 97.5) | 1.54E-2 |
| Corpus Callosum | 834 | 1.199E-3 |
| Dura | 1,667 (1,000 to 5,000) | 6E-4 |
| Eye | 200 (100 to 400) | 5E-3 |
| Fat | 2,500 (1,250 to 5,000) | 4E-4 |
| Muscle | 1,000 (200 to 1,800) | 1E-3 |
| Salivary Glands | 576 | 1.74E-3 |
| Scalp and Skin | 230 (115 to 345) | 4.25E-3 |
| Skull Hard Bone | 16,000 (8,000 to 40,000) | 6.25E-5 |
| Skull Soft Bone | 2,500 (1,250 to 3,750) | 4E-4 |
| Soft Tissue | 500 (250 to 750) | 2E-3 |
| Thalamus | 112 | 8.93E-3 |

*Mean values and lower and upper bounds of some of the tissues are included*

FIG. 1

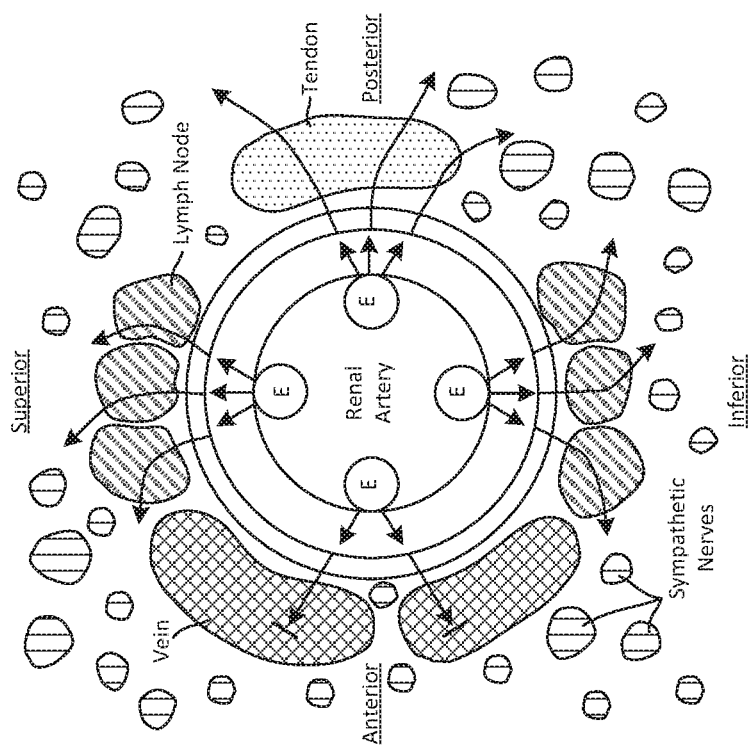

FIG. 2

SYSTEMS, DEVICES, AND ASSOCIATED METHODS FOR NEUROMODULATION WITH ENHANCED NERVE TARGETING

CROSS-REFERENCE

The present application claims the benefit of U.S. Provisional Patent Application No. 62/588,215, filed Nov. 17, 2017, the disclosure of which is incorporated herein by reference in its entirety.

TECHNICAL FIELD

The present technology is related to neuromodulation. In particular, various embodiments of the present technology are related to systems and methods for neuromodulation with enhanced nerve targeting.

BACKGROUND

The sympathetic nervous system (SNS) is a primarily involuntary bodily control system typically associated with stress responses. Fibers of the SNS extend through tissue in almost every organ system of the human body and can affect characteristics such as pupil diameter, gut motility, and urinary output. Such regulation can have adaptive utility in maintaining homeostasis or in preparing the body for rapid response to environmental factors. Chronic over-activation of the SNS, however, is a common maladaptive response that can drive the progression of many disease states. Excessive activation of the renal SNS in particular has been identified experimentally and in humans as a likely contributor to the complex pathophysiology of arrhythmias, hypertension, states of volume overload (e.g., heart failure), and progressive renal disease.

Sympathetic nerves of the kidneys terminate in the renal blood vessels, the juxtaglomerular apparatus, and the renal tubules, among other structures. Stimulation of the renal sympathetic nerves can cause, for example, increased renin release, increased sodium reabsorption, and reduced renal blood flow. These and other neural-regulated components of renal function are considerably stimulated in disease states characterized by heightened sympathetic tone. For example, reduced renal blood flow and glomerular filtration rate as a result of renal sympathetic efferent stimulation is likely a cornerstone of the loss of renal function in cardio-renal syndrome, (i.e., renal dysfunction as a progressive complication of chronic heart failure). Pharmacologic strategies to thwart the consequences of renal sympathetic stimulation include centrally-acting sympatholytic drugs, beta blockers (e.g., to reduce renin release), angiotensin-converting enzyme inhibitors and receptor blockers (e.g., to block the action of angiotensin II and aldosterone activation consequent to renin release), and diuretics (e.g., to counter the renal sympathetic mediated sodium and water retention). These pharmacologic strategies, however, have significant limitations including limited efficacy, compliance issues, side effects, and others.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

FIG. 1 is a table showing the electrical conduction properties of different types of tissue.

FIG. 2 is a schematic illustration showing the different electrical fields generated by ablation electrodes positioned at different locations within the lumen of a renal artery.

DETAILED DESCRIPTION

Figure 3:
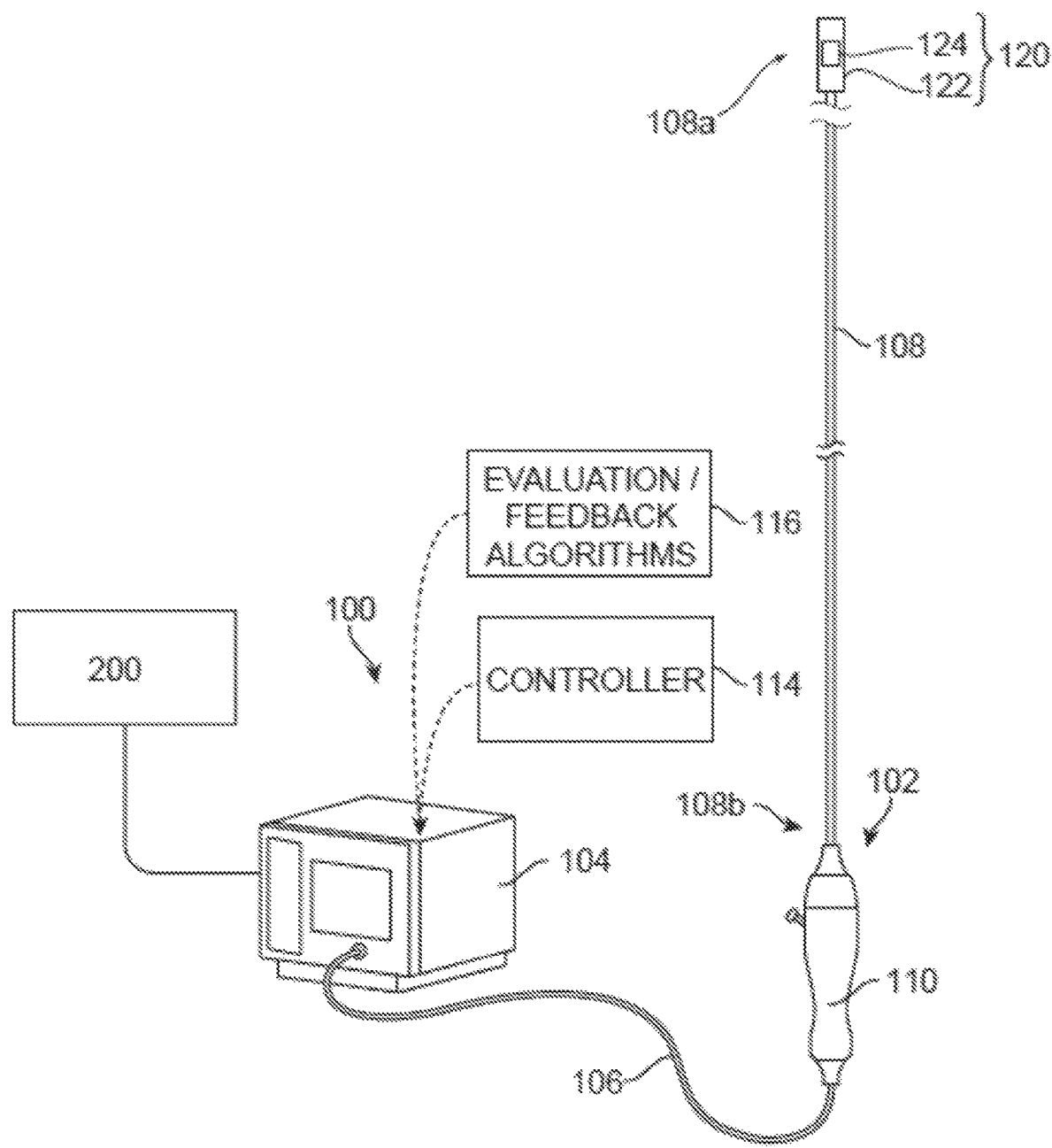
FIG. 3 is a partially schematic illustration of a neuromodulation system configured in accordance with some embodiments of the present technology.

The present technology is directed to devices, systems, and methods for neuromodulation, such as renal neuromodulation. In some embodiments, the present technology includes methods for selecting combinations of ablation electrodes and surface electrodes (e.g., reference electrodes) for the purpose of influencing the size, shape, and directionality of the electrical fields emanating from the ablation electrodes during treatment. The spatial and directional properties of the ablative energy directly affect the three-dimensional shape of the lesion(s) (i.e., damaged tissue) created by the ablative energy, as well as the position of the lesion(s) relative to the artery or other blood vessel in which the ablation electrodes are positioned during treatment. Accordingly, the present technology leverages the spatial relationships between ablation electrodes and reference electrodes to better concentrate the ablative energy on the targeted nerves, for a given local anatomy, and is thus expected to improve efficacy of neuromodulation treatment while minimizing/inhibiting the delivery of ablative energy to non-target tissue. As discussed in greater detail below, therapeutically-effective renal neuromodulation can include rendering neural fibers inert, inactive, or otherwise completely or partially reduced in function.

Specific details of several embodiments of the technology are described below with reference to FIGS. 1-14. The embodiments can include, for example, modulating nerves proximate (e.g., at or near) a renal artery, a renal vein, and/or other suitable structures. Although many of the embodiments are described herein with respect to electrically-induced approaches, other treatment modalities in addition to those described herein are within the scope of the present technology. Additionally, other embodiments of the present technology can have different configurations, components, or procedures than those described herein. A person of ordinary skill in the art, therefore, will accordingly understand that the technology can have other embodiments with additional elements and that the technology can have other embodiments without several of the features shown and described below with reference to FIGS. 1-14.

As used herein, the terms "distal" and "proximal" define a position or direction with respect to the treating clinician or clinician's control device (e.g., a handle assembly). "Distal" or "distally" can refer to a position distant from or in a direction away from the clinician or clinician's control device. "Proximal" and "proximally" can refer to a position near or in a direction toward the clinician or clinician's control device.

I. Overview

Some conventional renal denervation devices employ a multi-electrode, unipolar electrode system that delivers radio frequency (RF) energy to the endovascular surface of the renal artery (or other blood vessels) for the purpose of ablating nerves at the extravascular surface of the artery (or other blood vessels). An example of one such system is the multi-electrode Symplicity Spyral™ catheter along with a Symplicity G3™ generator. The catheter and generator are commercially available from Medtronic, Inc. The shape of the electric field and relative penetration depth of current densities strong enough to damage nerve tissue depend on several factors including, among others, the power and duration of energy delivery, the geometric shape of the electrodes, the electrode material, and the apposition of the electrodes against the vessel wall. The shape and current density of the electric field within the tissue also depends on the relative conductive properties of the tissue through which the current travels based on the relative three-dimensional conductivity of each individual tissue. FIG. 1, for example, is a table showing the electrical conduction properties of different types of tissue. In general, tissues that contain relatively more fluid, such as interstitial space, blood vessels, and lymph vessels, tend to conduct better than tissues with relatively less fluid, such as fat, tendon, and bone. FIG. 2 is a schematic illustration showing the different electrical fields generated by ablation electrodes positioned at different locations within the lumen of a renal artery. (Source: Esler; *Science Translational Medicine*, 29 Apr. 2015, Vol. 7, Issue 285.) As shown, the veins act as energy sinks and prevent RF energy from reaching the nerve target, while the lymph nodes and tendons draw the energy but redirect it. Accordingly, each unique electrode placement in a unique location within the artery of a unique individual is expected to create a unique electric field.

II. Neuromodulation Devices, Systems, and Methods of Use

FIG. 3 is a partially schematic illustration of a neuromodulation system 100 ("system 100") configured in accordance with some embodiments of the present technology. As shown in FIG. 3, the system 100 includes a neuromodulation catheter 102, a console 104, and a cable 106 extending therebetween. The system 100 further includes a plurality of patch or reference electrodes 200 (e.g., return or neutral electrodes) configured to be positioned on the patient's skin and electrically coupled to the console 104.

The neuromodulation catheter 102 can include an elongated shaft 108 having a proximal portion 108b, a distal portion 108a, a handle 110 operably connected to the shaft 108 at the proximal portion 108b, and a neuromodulation assembly 120 operably connected to the shaft 108 at the distal portion 108a. The shaft 108 and the neuromodulation assembly 120 can be 2, 3, 4, 5, 6, or 7 French or another suitable size. As shown schematically in FIG. 3, the neuromodulation assembly 120 can include a support structure 122 carrying an array of two or more ablation electrodes 124 spaced apart along the shaft 108. The ablation electrodes 124 can be configured to apply electrical stimuli (e.g., RF energy) to target sites at or proximate to vessels within a patient, temporarily stun nerves, deliver neuromodulation energy to target sites, and/or detect local tissue impedance. In some embodiments, the ablation electrodes 124 may be shaped to improve/enhance contact with the vessel wall. For example, the ablation electrodes 124 may be shaped such that an outer or engagement surface of the individual electrodes more closely matches the shape of the vessel wall to ensure maximum wall contact (and thereby enhance reliable energy delivery).

The distal portion 108a of the shaft 108 is configured to be moved within a lumen of a human patient and locate the neuromodulation assembly 120 at a target site within or otherwise proximate to the lumen. For example, the shaft 108 can be configured to position the neuromodulation assembly 120 within a blood vessel, a duct, an airway, or another naturally occurring lumen within the human body. In certain embodiments, intravascular delivery of the neuromodulation assembly 120 includes percutaneously inserting a guide wire (not shown) into a body lumen of a patient and moving the shaft 108 and/or the neuromodulation assembly 120 along the guide wire until the neuromodulation assembly 120 reaches a target site (e.g., a renal artery). For example, the distal end of the neuromodulation assembly 120 may define a passageway for engaging the guide wire for delivery of the neuromodulation assembly 120 using over-the-wire (OTW) or rapid exchange (RX) techniques. In other embodiments, the neuromodulation catheter 102 can be a steerable or non-steerable device configured for use without a guide wire. In still other embodiments, the neuromodulation catheter 102 can be configured for delivery via a guide catheter or sheath (not shown).

Once positioned at the target site, the neuromodulation assembly 120 can be configured to apply stimuli, detect resultant hemodynamic responses, and provide or facilitate neuromodulation therapy at the target site (e.g., using the ablation electrodes 124 and/or other energy delivery elements). For example, the neuromodulation assembly 120 can detect vessel impedance via the ablation electrodes 124, blood flow via a flow sensing element (e.g., a Doppler velocity sensing element), local blood pressure within the vessel via a pressure transducer or other pressure sensing element, and/or other hemodynamic parameters. In some embodiments, the neuromodulation assembly 120 can detect vessel impedance via sensing elements separate from the ablation electrodes 124. In such embodiments, the neuromodulation assembly 102 may detect impedance with one or both of the sensing elements and the ablation electrodes 124. The detected responses can be transmitted to the console 104 and/or another device external to the patient. The console 104 can be configured to receive and store the recorded impedance measurements for further use by a clinician or operator. For example, a clinician can use the impedance measurements received by the console 104 to select combinations of ablation electrodes and reference electrodes, as described in greater detail below.

The console 104 can be configured to control, monitor, supply, and/or otherwise support operation of the neuromodulation catheter 102. The console 104 can further be configured to generate a selected form and/or magnitude of energy for delivery to tissue at the target site via the neuromodulation assembly 120, and therefore the console 104 may have different configurations depending on the treatment modality of the neuromodulation catheter 102. For example, the console 104 can include an energy generator (not shown) configured to generate RF energy. In some embodiments, the system 100 may be configured to deliver a monopolar electric field via one or more of the ablation electrodes 124 and/or bipolar energy between selected combination(s) of ablation electrodes 124. The reference electrodes 200 may be electrically connected to the console 104 and positioned at the skin of the patient at multiple locations to help direct and shape the electric field generated by the ablation electrodes 124 (as discussed in greater detail below with reference to FIG. 5). In embodiments including multiple ablation electrodes 124, the ablation electrodes 124 may deliver power independently (i.e., may be used in a monopolar fashion), either simultaneously, selectively, or sequentially, and/or may deliver power between any desired combination of the ablation electrodes 124 (i.e., may be used in a bipolar fashion). In addition, an operator optionally may be permitted to choose which ablation electrodes 124 are used for power delivery based, at least in part, on local anatomic features or other specific feedback, in order to form highly customized lesion(s) within the renal artery, as desired. One or more sensing elements (not shown), such as one or more temperature (e.g., thermocouple, thermistor, etc.), pressure, optical, flow, chemical, and/or other sensing elements, may be located proximate to, within, or integral with the ablation electrodes 124. The sensing element(s) and the ablation electrodes 124 can be connected to one or more supply wires (not shown) that transmit signals from the sensing element(s) and/or convey energy to the ablation electrodes 124. Feedback from such signals may processed by the module, presented to the operator, and used by the operator to inform on which available electrode-reference combination(s) to choose.

In various embodiments, the system 100 can further include a controller 114 communicatively coupled to the neuromodulation catheter 102. The controller 114 can be configured to initiate, terminate, and/or adjust operation of one or more components (e.g., the ablation electrodes 124) of the neuromodulation catheter 102 directly and/or via the console 104. For example, as described in greater detail below, the controller 114 may be configured to continuously or intermittently monitor the impedance between each of the ablation electrodes 124 and each of the reference electrodes 200 and, based on those measurements, select particular ablation electrode 124/reference electrode 200 groupings that provide optimal electric fields for efficacious neuromodulation therapy. The controller 114 may also be configured to further adjust delivered power based on anatomical and/or sensor feedback.

In some embodiments, the controller 114 can be a component separated from the console 104, such as within the handle 110, along the cable 106, etc. The controller 114 can be configured to execute one or more automated control algorithms and/or to receive control instructions from an operator. Further, the console 104 can be configured to provide feedback to an operator before, during, and/or after a treatment procedure via an evaluation/feedback algorithm 116 (e.g., such as changing ablation electrode 124/reference electrode 200 groupings in response to impedance measurements).

Figure 4:
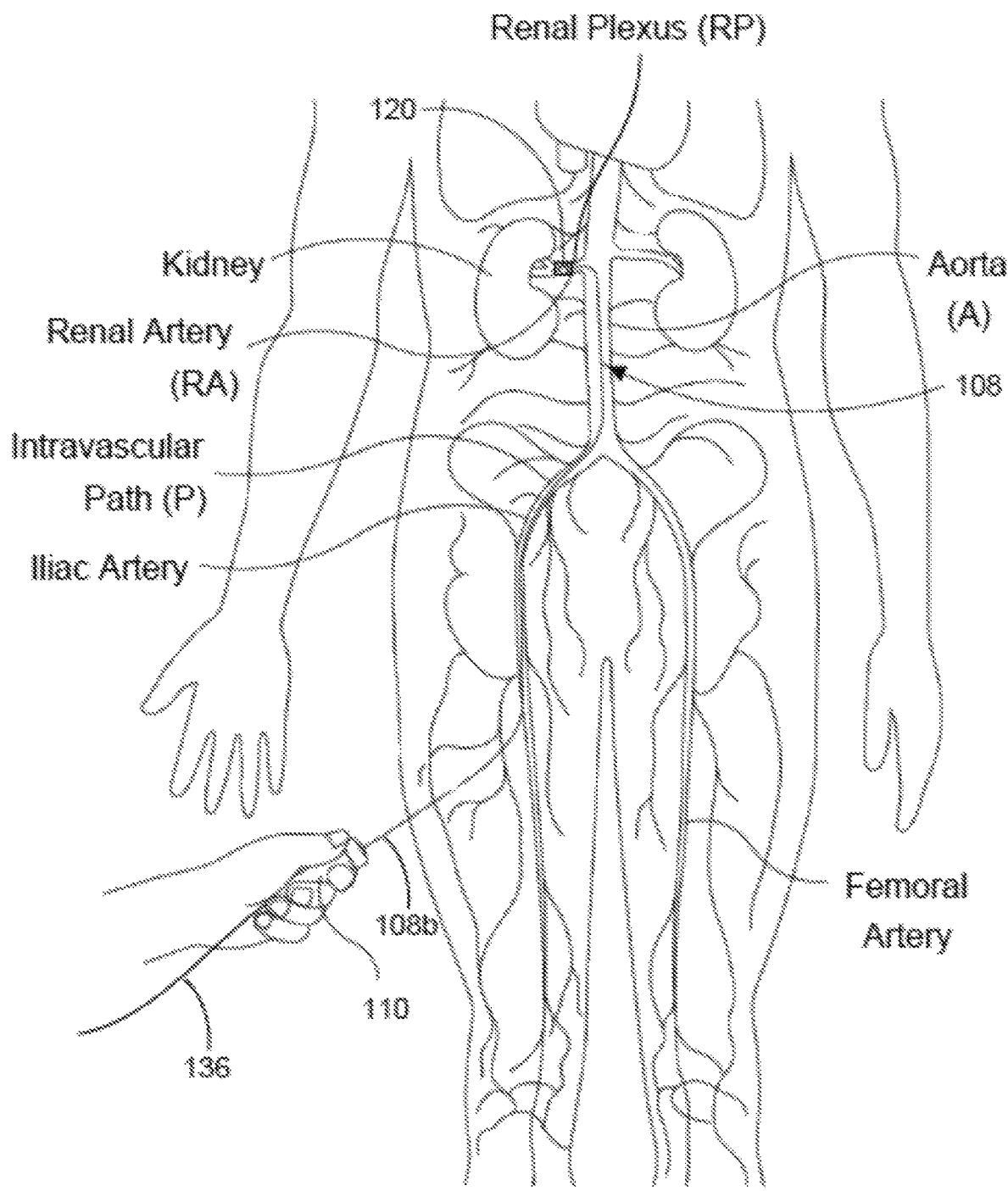
FIGS. 4 and 5 illustrate modulating renal nerves with the system of FIG. 3 in accordance with some embodiments of the present technology.

FIG. 4 (with additional reference to FIG. 3) illustrates gaining access to renal nerves in accordance with some embodiments of the present technology. The neuromodulation catheter 102 provides access to the renal plexus RP through an intravascular path P, such as a percutaneous access site in the femoral (illustrated), brachial, radial, or axillary artery to a targeted treatment site within a respective renal artery RA. By manipulating the proximal portion 108b of the shaft 108 from outside the intravascular path P, a clinician may advance the shaft 108 through the sometimes tortuous intravascular path P and remotely manipulate the distal portion 108a (FIG. 3) of the shaft 108. In the embodiment illustrated in FIG. 4, the neuromodulation assembly 120 is delivered intravascularly to the treatment site using a guide wire 136 in an OTW technique. As noted previously, the distal end of the neuromodulation assembly 120 may define a passageway for receiving the guide wire 136 for delivery of the neuromodulation catheter 102 using either OTW or RX techniques. At the treatment site, the guide wire 136 can be at least partially withdrawn or removed, and the neuromodulation assembly 120 can transform or otherwise be moved to a deployed arrangement for recording neural activity and/or delivering energy at the treatment site. In other embodiments, the neuromodulation assembly 120 may be delivered to the treatment site within a guide sheath (not shown) with or without using the guide wire 136. When the neuromodulation assembly 120 is at the target site, the guide sheath may be at least partially withdrawn or retracted and the neuromodulation assembly 120 can be transformed into the deployed arrangement. In still other embodiments, the shaft 108 may be steerable itself such that the neuromodulation assembly 120 may be delivered to the treatment site without the aid of the guide wire 136 and/or guide sheath.

Image guidance, e.g., computed tomography (CT), fluoroscopy, intravascular ultrasound (IVUS), optical coherence tomography (OCT), intracardiac echocardiography (ICE), or another suitable guidance modality, or combinations thereof, may be used to aid the clinician's positioning and manipulation of the neuromodulation assembly 120. For example, a fluoroscopy system (e.g., including a flat-panel detector, x-ray, or c-arm) can be rotated to accurately visualize and identify the target treatment site. In other embodiments, the treatment site can be determined using IVUS, OCT, and/or other suitable image mapping modalities that can correlate the target treatment site with an identifiable anatomical structure (e.g., a spinal feature) and/or a radiopaque ruler (e.g., positioned under or on the patient) before delivering the neuromodulation assembly 120. Further, in some embodiments, image guidance components (e.g., IVUS, OCT) may be integrated with the neuromodulation catheter 102 and/or run in parallel with the neuromodulation catheter 102 to provide image guidance during positioning of the neuromodulation assembly 120. For example, image guidance components (e.g., IVUS or OCT) can be coupled to the neuromodulation assembly 120 to provide three-dimensional images of the vasculature proximate the target site to facilitate positioning or deploying the multi-electrode assembly within the target renal blood vessel.

Figure 5:
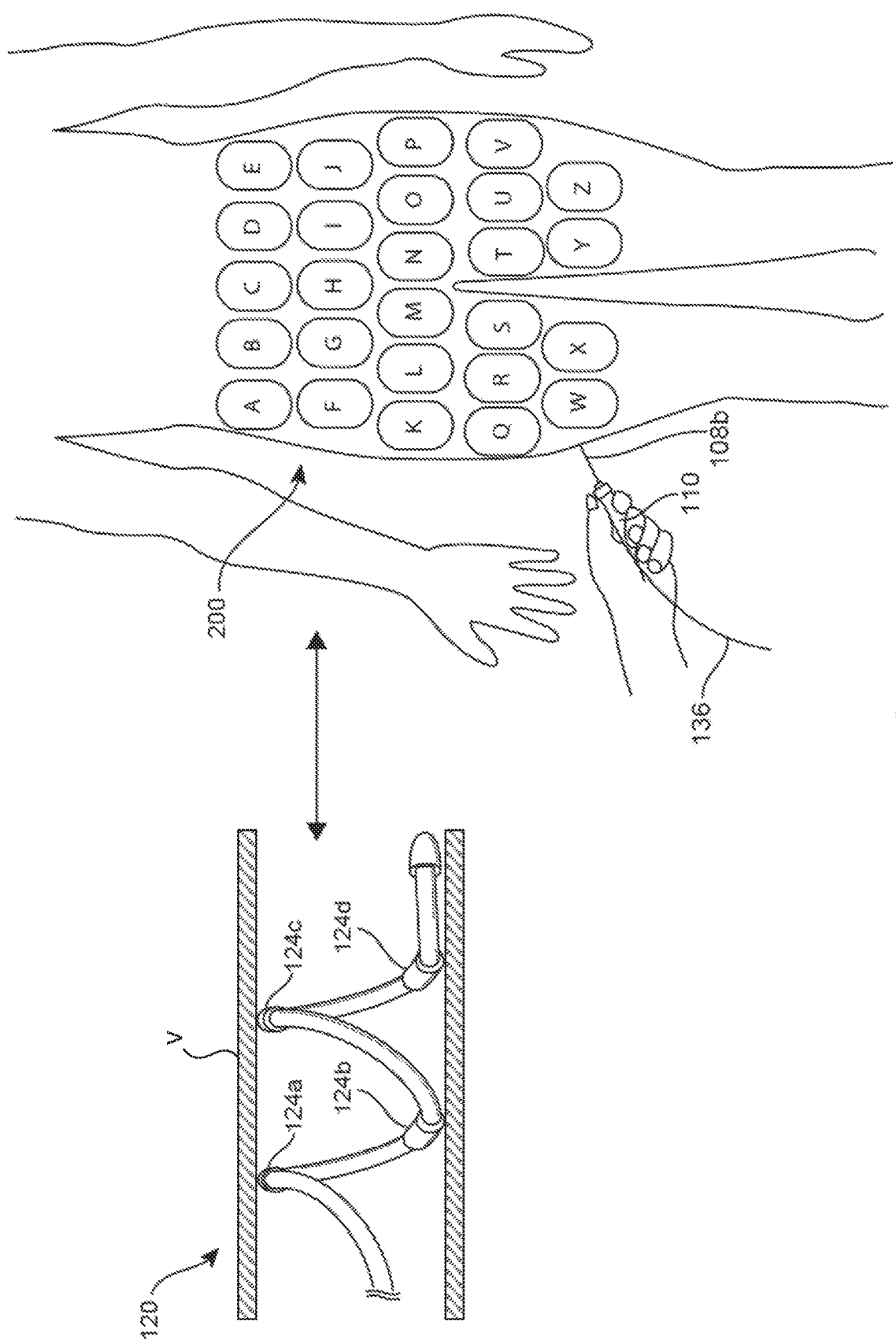

As shown schematically in FIG. 5, a plurality of reference electrodes 200 (individually labeled A-Z) may be positioned about the patient's abdominal area while the neuromodulation assembly 120 is positioned within the patient's blood vessel V (e.g., renal artery). The reference electrodes 200 may be positioned on the patient before, during, and/or after placement of the neuromodulation assembly 120 in the blood vessel V. In some embodiments, the neuromodulation assembly 120 may include first, second, third, and fourth ablation electrodes 124a-124d (referred to collectively as "ablation electrodes 124"), for example as shown in FIG. 5. In other embodiments, however, the neuromodulation assembly 120 may include more or fewer ablation electrodes 124 (e.g., two ablation electrodes, three ablation electrodes, five ablation electrodes, six ablation electrodes, etc.).

Although the reference electrodes 200 are shown positioned at the abdomen and upper leg region of the patient, in some embodiments one or more of the reference electrodes 200 may be positioned elsewhere on the patient's body, such as the patient's arms, lower legs, and upper torso, as well as at the backside of the patient. In additional embodiments, one or more reference electrodes 200 may also be carried on the catheter 102, guide catheter, guide wire, introducer, and/or a separate reference electrode catheter configured to be positioned at a desired location within the patient's vasculature (e.g., renal vein, renal artery, etc.) or a suitable body lumen (e.g., ureter). Moreover, any number of reference electrodes 200 may be used to achieve a desired specific or alternate energy delivery profile, such as one reference electrode, two reference electrodes, five reference electrodes, 15 reference electrodes, 30 reference electrodes, 100 reference electrodes, etc.

Figure 6:
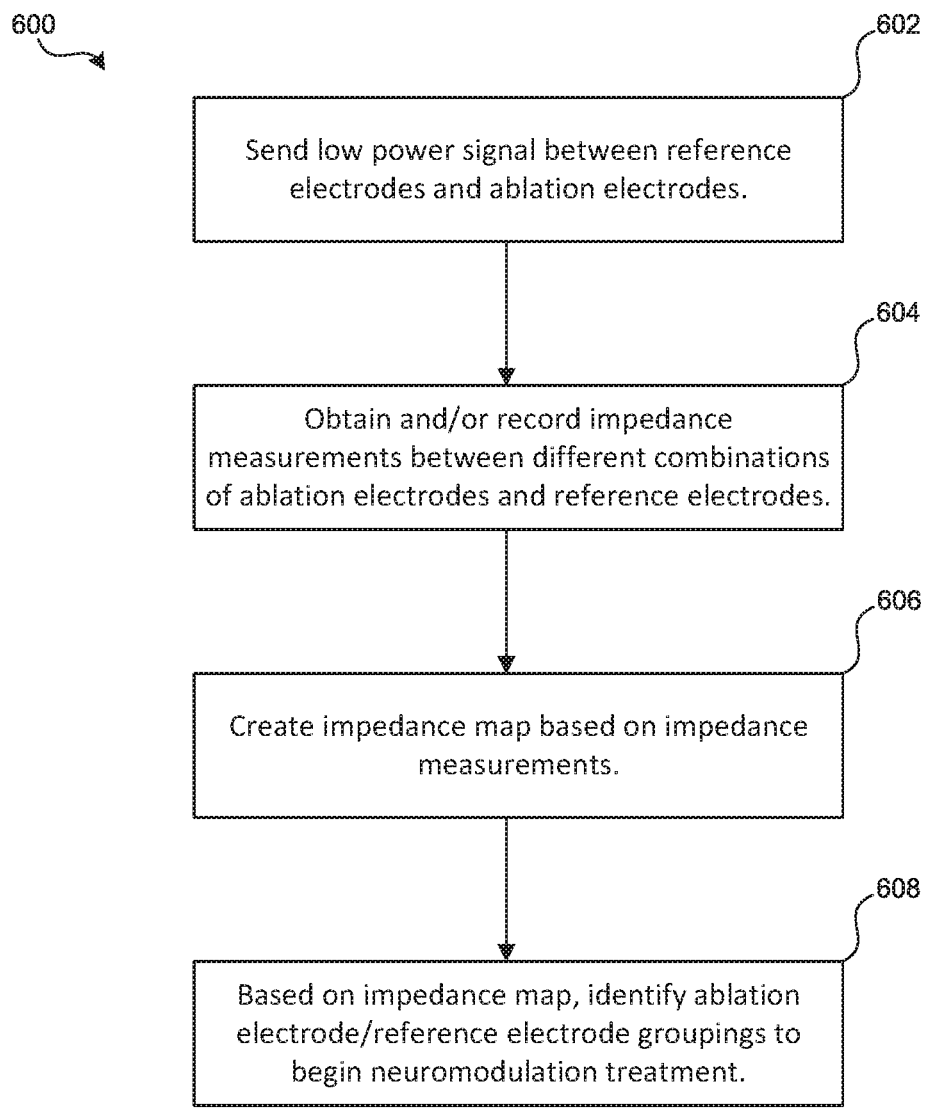
FIG. 6 is a block diagram illustrating a method of using ablation electrodes and reference electrodes to create an impedance map in accordance with some embodiments of the present technology.

FIG. 6 is a block diagram illustrating a method 600 of mapping the electrical environment surrounding the neuromodulation assembly 120 prior to neuromodulation therapy, in accordance with some embodiments of the present technology. Referring to FIGS. 5 and 6 together, according to some methods of the present technology, a low power signal may be sent between one or more of the ablation electrodes 124 and one or more of the reference electrodes 200 before energy delivery (block 602), and the resulting impedance of each combination may be measured (e.g., via the ablation electrodes 124) (block 604) to create a rough impedance map of the anatomical environment (and its conductivity profile) at or near the treatment site (block 606). For example, a low power signal may be sent between the first ablation electrode 124a and each of the reference electrodes (A-Z), and all 26 of those measurements may be stored at the controller 114 (FIG. 3). The same process may be repeated for any of the second-fourth ablation electrodes 124b-d. In some embodiments, impedance measurements may be obtained for less than every combination of ablation electrode 124 and reference electrode 200. The obtained impedance measurements can be organized to form an impedance map that informs the clinician of the effects of the local anatomy on the shape of the electric field induced between the ablation electrodes 124 and reference electrodes 200. Based on the impedance map, as well as images already obtained of the local anatomy and/or known tissue electrical conduction properties (see FIG. 1), the clinician may select particular reference electrode/ablation electrode combinations to optimize the direction and/or three-dimensional shape of the electric field during subsequent energy delivery (block 608). In some embodiments, the controller 114 (FIG. 3) automatically identifies certain ablation electrode/reference electrode groups based on the mapping and/or automatically begins treatment using the identified ablation electrode/reference electrode groupings. In some embodiments, identification of the optimal ablation electrode 124/reference electrode 200 combinations includes comparing (manually and/or automatically by the controller 114) the impedance measurements to one another and/or to a predetermined threshold. As used herein, a "threshold" refers to a single value or a range of values. Relatively lower impedance pathways, for example, may indicate a more direct route for RF current from the electrode to the respective ground electrode, since blood is more conductive than muscle. Hence, low impedance pathways may be the result of more current being shunted away via the blood vessel, rather than being forced through the adventitia where the nerves reside.

Figure 7:
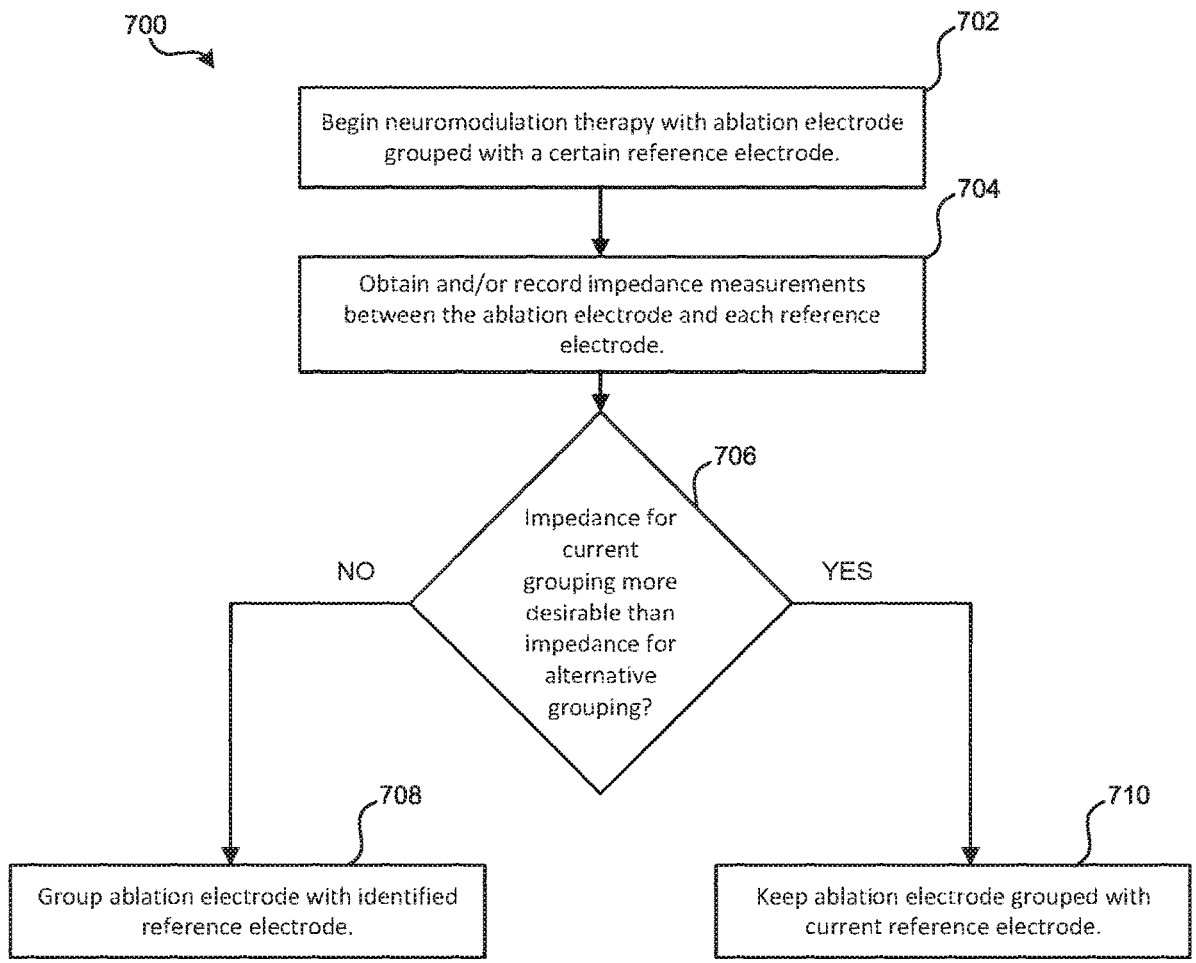
FIG. 7 is a block diagram illustrating a method of modulating renal nerves in accordance with some embodiments of the present technology.

FIG. 7 is a block diagram illustrating a method 700 of evaluating the efficacy of different electrode groupings via impedance measurements obtained in real-time during neuromodulation therapy. For example, in some embodiments, with or without generating an impedance map prior to energy delivery, the clinician may begin neuromodulation therapy (block 702) by delivering energy from the ablation electrodes 124 and/or other energy delivery elements to target tissue to induce one or more desired neuromodulating effects on localized regions of the renal artery RA and adjacent regions of the renal plexus RP, which lay intimately within, adjacent to, or in close proximity to the adventitia of the renal artery RA. The purposeful application of the energy may achieve neuromodulation along all or at least a portion of the renal plexus RP.

During energy delivery, the controller 114 may continuously or intermittently obtain impedance measurements for a given ablation electrode 124 relative to each of the reference electrodes 200, and automatically compare these impedance measurements to one another and/or to a predetermined threshold to determine which reference electrode 200 provides the optimal electrical field profile for the ablation electrode 124. For example, as shown in FIG. 7, energy delivery may begin with each ablation electrode 124 grouped with a particular reference electrode 200 (block 702). In some embodiments, each ablation electrode 124 may be initially grouped with a different reference electrode(s) 200, and in some embodiments some or all of the ablation electrodes 124 may be initially grouped with the same reference electrode 200. During energy delivery, the controller 114 (FIG. 3) may continuously or intermittently obtain impedance measurements between each ablation electrode 124 and each of the reference electrodes (A-Z) (block 704) and compare the impedance measurements obtained for a given ablation electrode to one another and/or to a predetermined threshold (block 706). Based on this comparison, the controller 114 may automatically select the ablation electrode 124/reference electrode 200 grouping that provides the optimal electrical field to achieve a desired treatment profile. For instance, if the comparison determines that the ablation electrode 124 is not currently grouped with the reference electrode 200 that would provide the optimal current path, the controller 114 may automatically stop sending current between the ablation electrode 124 and the currently-paired reference electrode 200 and start sending current between the ablation electrode 124 and the different reference electrode 200 (block 708). Likewise, if the comparison determines that the ablation electrode 124 is already grouped with the reference electrode 200 that provides the optimal current path (based on impedance measurements or some other parameter that reflect current usage to infer successful energy delivery to the target nerves), the controller 114 may continue sending current between the ablation electrode 124 and the present reference electrode 200 (block 710). The foregoing process may be executed (simultaneously or sequentially) for any of the ablation electrodes 124a-d.

In other embodiments, the controller 114 may be configured to automatically toggle the reference electrode(s)

between two or more ground patches, regardless of impedance, during treatment. For example, the controller 114 may toggle between various ablation electrode/reference electrode groups based on predetermined time limits (e.g., 10 second cycles for each combination). In still other embodiments, the controller 114 may be configured to automatically and/or manually toggle between different electrode groupings based on still other parameters (in addition to, or in lieu of, impedance or time).

In addition to reference electrode/ablation electrode placement, the neuromodulating effects are generally a function of, at least in part, power, time, contact between the energy delivery elements and the vessel wall, and blood flow through the vessel. The neuromodulating effects may include denervation, thermal ablation, and/or non-ablative thermal alteration or damage (e.g., via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature may be above body temperature (e.g., approximately 37° C.) but less than about 45° C. for non-ablative thermal alteration, or the target temperature may be about 45° C. or higher for the ablative thermal alteration. Desired non-thermal neuromodulation effects may include altering the electrical signals transmitted in a nerve.

Figure 8B:
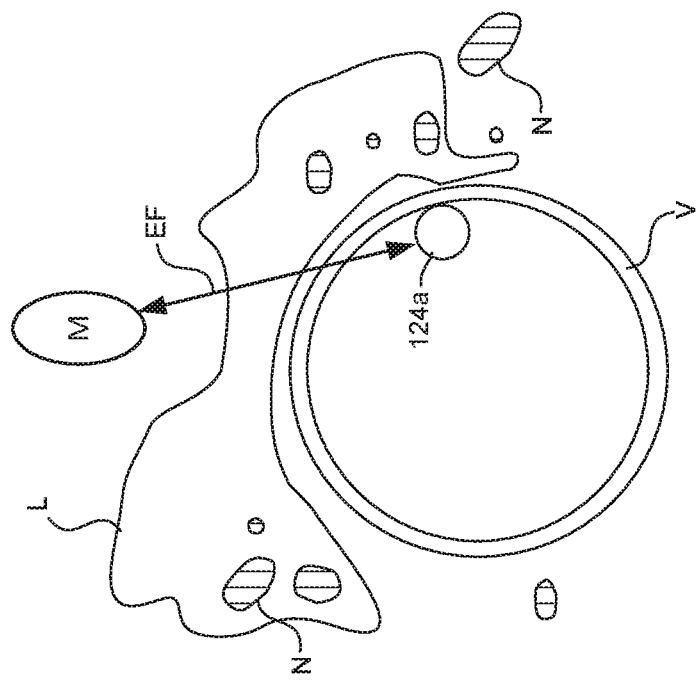
FIGS. 8A and 8B are schematic representations showing the effects of different electrode groupings on lesion size, shape, and position.
Figure 8A:
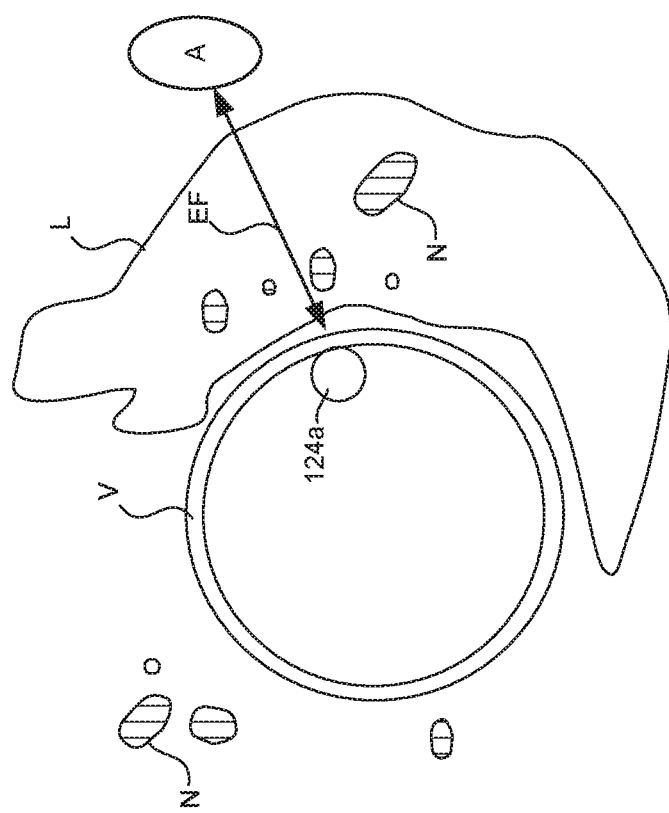

By way of example, FIGS. 8A and 8B are schematic representations showing the effects of different ablation electrode 124/reference electrode 200 groupings on lesion size, shape, and position. FIG. 8A, for example, shows a lesion L caused by sending neuromodulation current between the first ablation electrode 124a and reference electrode A (positioned at a first location on the patient's body). As shown in FIG. 8A, the lesion L is positioned generally along the right half circumference of the blood vessel V and thus captures a first set of nerves N at that side of the vessel V. In comparison, FIG. 8B shows the lesion L caused by sending neuromodulation current between the first ablation electrode 124a and reference electrode M (positioned at a second location on the patient's body spaced apart from the first location). As shown in FIG. 8B, the lesion L is positioned generally along the top half circumference of the blood vessel V and thus captures a second set of nerves N at that side of the vessel V. Also, as shown in FIGS. 8A and 8B, in addition to the first and second lesions being located at different positions relative to the blood vessel V, the first and second lesions are also different shapes and enclose different volumes.

In some embodiments, a temperature at one or more of the ablation electrodes 124 may be measured (instead of or in addition to measuring impedance) in addition to or in substitution of impedance. In additional embodiments, electroencephalogram (EEG) monitoring and/or blood chemistry may also be utilized to provide real time patient feedback during therapy.

III. Renal Neuromodulation

Renal neuromodulation is the partial or complete incapacitation or other effective disruption of nerves of the kidneys (e.g., nerves terminating in the kidneys or in structures closely associated with the kidneys). In particular, renal neuromodulation can include inhibiting, reducing, and/or blocking neural communication along neural fibers (e.g., efferent and/or afferent neural fibers) of the kidneys. Such incapacitation can be long-term (e.g., permanent or for periods of months, years, or decades) or short-term (e.g., for periods of minutes, hours, days, or weeks). Renal neuromodulation is expected to contribute to the systemic reduction of sympathetic tone or drive and/or to benefit at least some specific organs and/or other bodily structures innervated by sympathetic nerves. Accordingly, renal neuromodulation is expected to be useful in treating clinical conditions associated with systemic sympathetic overactivity or hyperactivity, particularly conditions associated with central sympathetic overstimulation. For example, renal neuromodulation is expected to efficaciously treat hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, polycystic kidney disease, polycystic ovary syndrome, osteoporosis, erectile dysfunction, and sudden death, among other conditions.

Renal neuromodulation can be electrically-induced, thermally-induced, chemically-induced, or induced in another suitable manner or combination of manners at one or more suitable target sites during a treatment procedure. The target site can be within or otherwise proximate to a renal lumen (e.g., a renal artery, a ureter, a renal pelvis, a major renal calyx, a minor renal calyx, or another suitable structure), and the treated tissue can include tissue at least proximate to a wall of the renal lumen. For example, with regard to a renal artery, a treatment procedure can include modulating nerves in the renal plexus, which lay intimately within or adjacent to the adventitia of the renal artery.

Renal neuromodulation can include an electrode-based or transducer-based treatment modality alone or in combination with another treatment modality. As discussed herein, for example, electrode-based or transducer-based treatment can include delivering electricity and/or another form of energy to tissue at a treatment location to stimulate and/or heat the tissue in a manner that modulates neural function. For example, sufficiently stimulating and/or heating at least a portion of a sympathetic renal nerve can slow or potentially block conduction of neural signals to produce a prolonged or permanent reduction in renal sympathetic activity. A variety of suitable types of energy can be used to stimulate and/or heat tissue at a treatment location. For example, neuromodulation in accordance with embodiments of the present technology can include delivering RF energy, pulsed electrical energy, or another suitable type of energy in combination with the electrical energy. An electrode or transducer used to deliver this energy can be used alone or with other electrodes or transducers in a multi-electrode or multi-transducer array. Furthermore, the energy can be applied from within the body (e.g., within the vasculature or other body lumens in a catheter-based approach) and/or from outside the body (e.g., via an applicator positioned outside the body). Furthermore, energy can be used to reduce damage to non-targeted tissue when targeted tissue adjacent to the non-targeted tissue is subjected to neuromodulating cooling.

In certain embodiments, neuromodulation may utilize one or more devices including, for example, catheter devices such as the Symplicity™ catheter or Symplicity Spyral™ catheter mentioned previously (Medtronic, Inc.). Other suitable thermal devices are described in U.S. Pat. Nos. 7,653,438, 8,347,891, and U.S. patent application Ser. No. 13/279,205, filed Oct. 21, 2011. Other suitable devices and technologies are described in U.S. patent application Ser. No. 13/279,330, filed Oct. 23, 2011, International Patent Application No. PCT/US2015/021835, filed Mar. 20, 2015, and International Patent Application No. PCT/US2015/013029, filed Jan. 27, 2015. Further, electrodes (or other energy delivery elements) can be used alone or with other electrodes in a multi-electrode array. Examples of suitable multi-electrode devices are described in U.S. patent application Ser. No. 13/281,360, filed Oct. 25, 2011, and U.S. Pat. No. 8,888,773. All of the foregoing patent references are incorporated herein by reference in their entireties.

Thermal effects can include both thermal ablation and/or non-ablative thermal alteration or damage (e.g., via sustained heating and/or resistive heating) to partially or completely disrupt the ability of a nerve to transmit a signal. Such thermal effects can include the heating effects associated with electrode-based or transducer-based treatment. For example, a treatment procedure can include raising the temperature of target neural fibers to a target temperature above a first threshold to achieve non-ablative alteration, or above a second, higher threshold to achieve ablation. The target temperature can be higher than about body temperature (e.g., about 37° C.) but less than about 45° C. for non-ablative alteration, and the target temperature can be higher than about 45° C. for ablation. Heating tissue to a temperature between about body temperature and about 45° C. can induce non-ablative alteration, for example, via moderate heating of target neural fibers or of vascular or luminal structures that perfuse the target neural fibers. In cases where vascular structures are affected, the target neural fibers can be denied perfusion resulting in necrosis of the neural tissue. Heating tissue to a target temperature higher than about 45° C. (e.g., higher than about 60° C.) can induce ablation, for example, via substantial heating of target neural fibers or of vascular or luminal structures that perfuse the target fibers. In some patients, it can be desirable to heat tissue to temperatures that are sufficient to ablate the target neural fibers or the vascular or luminal structures, but less than about 90° C. (e.g., less than about 85° C., less than about 80° C., or less than about 75° C.). Other embodiments can include heating tissue to a variety of other suitable temperatures.

IV. Related Anatomy and Physiology

As noted previously, the sympathetic nervous system (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to physiological features as diverse as pupil diameter, gut motility, and urinary output. This response is also known as sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

A. The Sympathetic Chain

Figure 9:
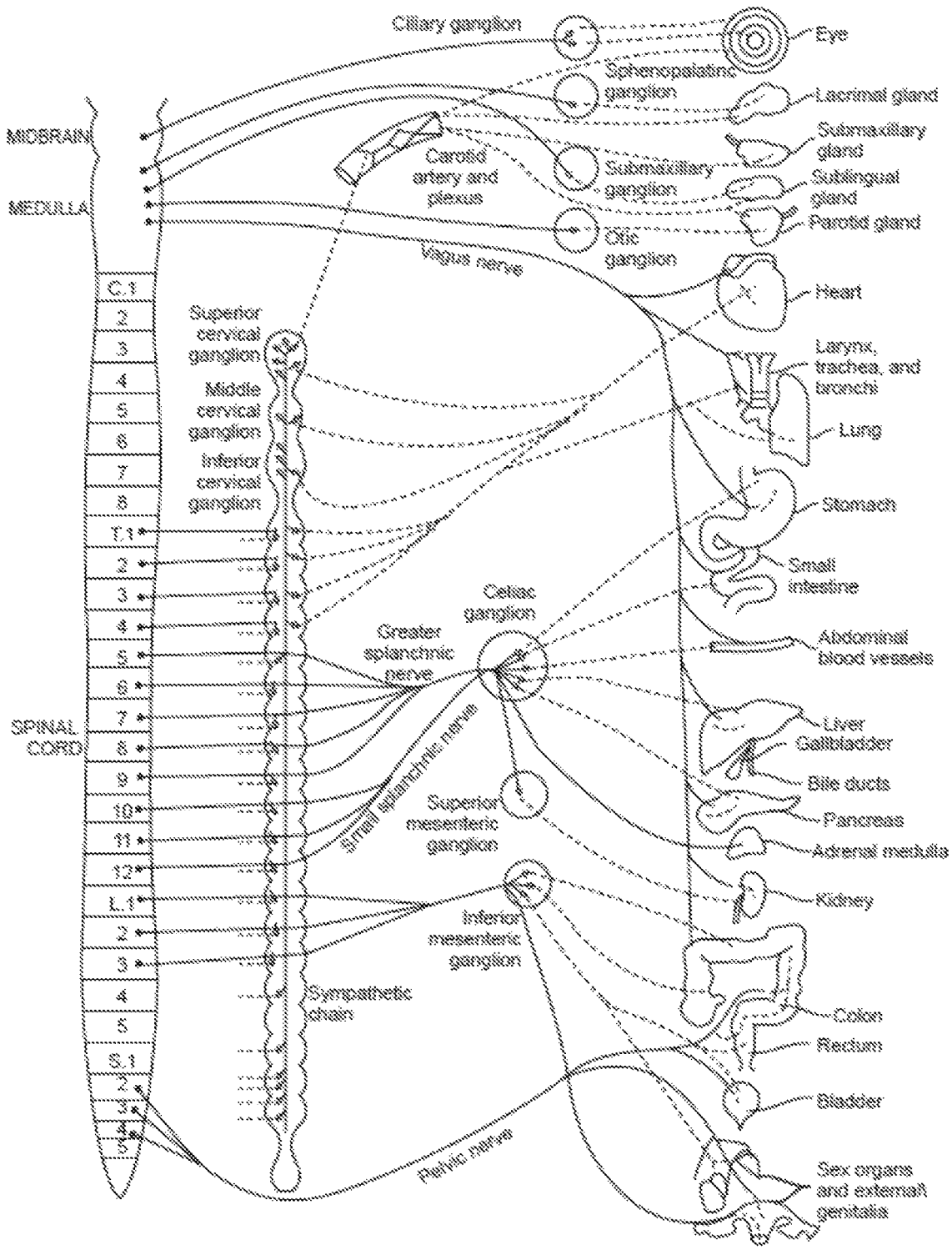
FIG. 9 is a conceptual illustration of the sympathetic nervous system (SNS) and how the brain communicates with the body via the SNS.

As shown in FIG. 9, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensing element) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifurcation) ganglia extending alongside the spinal column.

In order to reach the target organs and glands, the axons should travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia, discussed above. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

1. Innervation of the Kidneys

Figure 10:
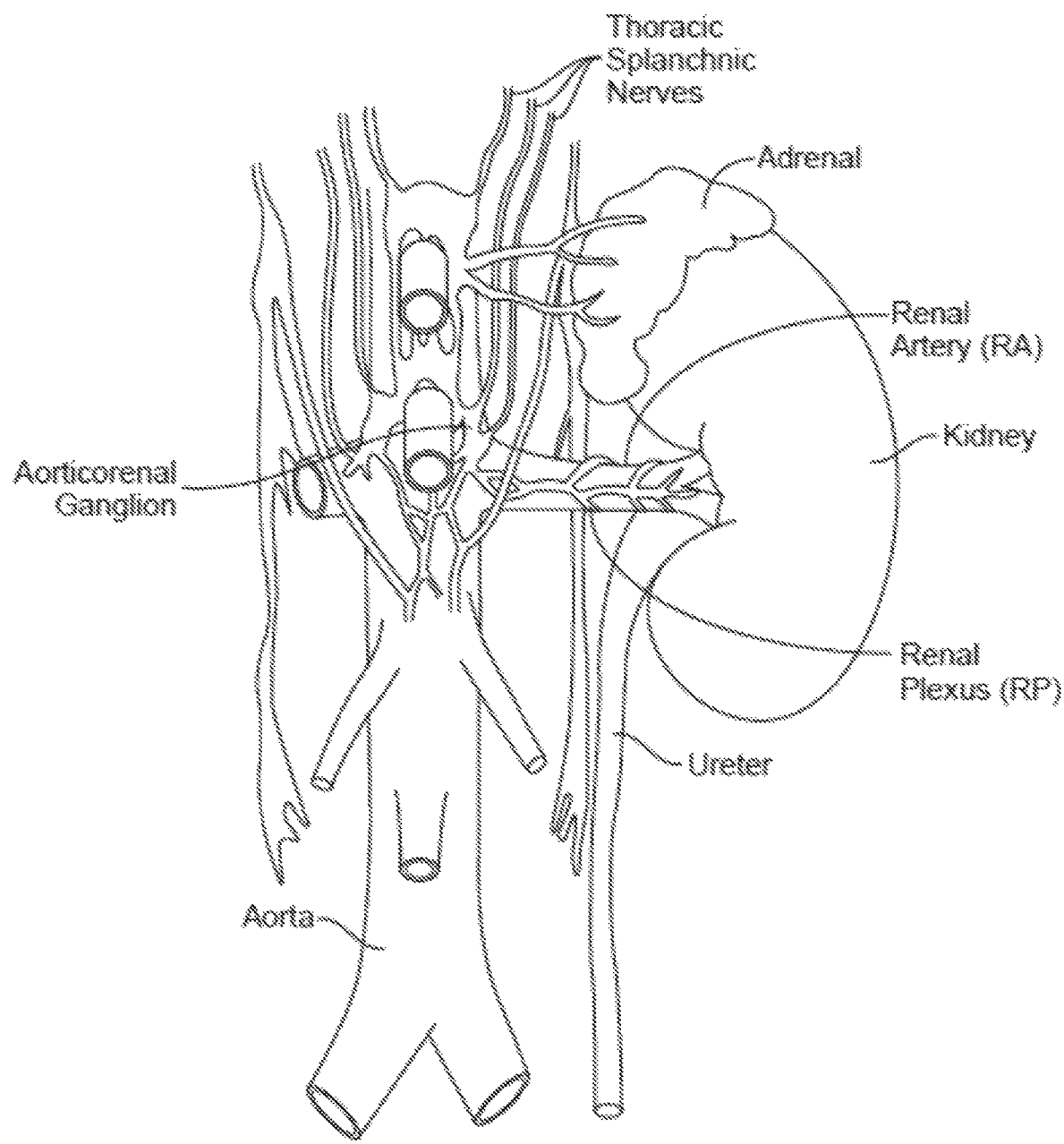
FIG. 10 is an enlarged anatomic view of nerves innervating a left kidney to form the renal plexus surrounding the left renal artery.

As FIG. 10 shows, the kidney is innervated by the renal plexus (RP), which is intimately associated with the renal artery. The renal plexus (RP) is an autonomic plexus that surrounds the renal artery and is embedded within the adventitia of the renal artery. The renal plexus (RP) extends along the renal artery until it arrives at the substance of the kidney. Fibers contributing to the renal plexus (RP) arise from the celiac ganglion, the superior mesenteric ganglion, the aorticorenal ganglion and the aortic plexus. The renal plexus (RP), also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus (RP) and are distributed to the renal vasculature.

2. Renal Sympathetic Neural Activity

Messages travel through the SNS in a bidirectional flow. Efferent messages may trigger changes in different parts of the body simultaneously. For example, the sympathetic nervous system may accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensing element receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensing element afferent signals originating from the diseased kidneys are major contributors to initiating and sustaining elevated central sympathetic outflow in this patient group; this facilitates the occurrence of the well-known adverse consequences of chronic sympathetic over activity, such as hypertension, left ventricular hypertrophy, ventricular arrhythmias, sudden cardiac death, insulin resistance, diabetes, and metabolic syndrome.

(i) Renal Sympathetic Efferent Activity

Sympathetic nerves to the kidneys terminate in the blood vessels, the juxtaglomerular apparatus and the renal tubules. Stimulation of the renal sympathetic nerves causes increased renin release, increased sodium ($Na^+$) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

(ii) Renal Sensory Afferent Nerve Activity

Figure 11:
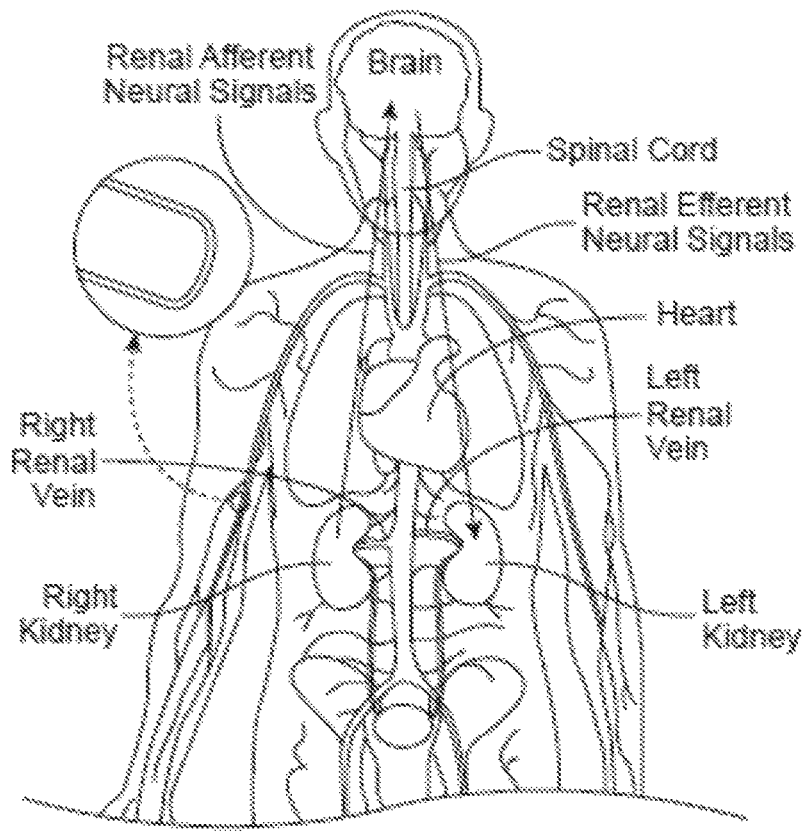
FIGS. 11 and 12 are anatomic and conceptual views, respectively, of a human body depicting neural efferent and afferent communication between the brain and kidneys.
Figure 12:
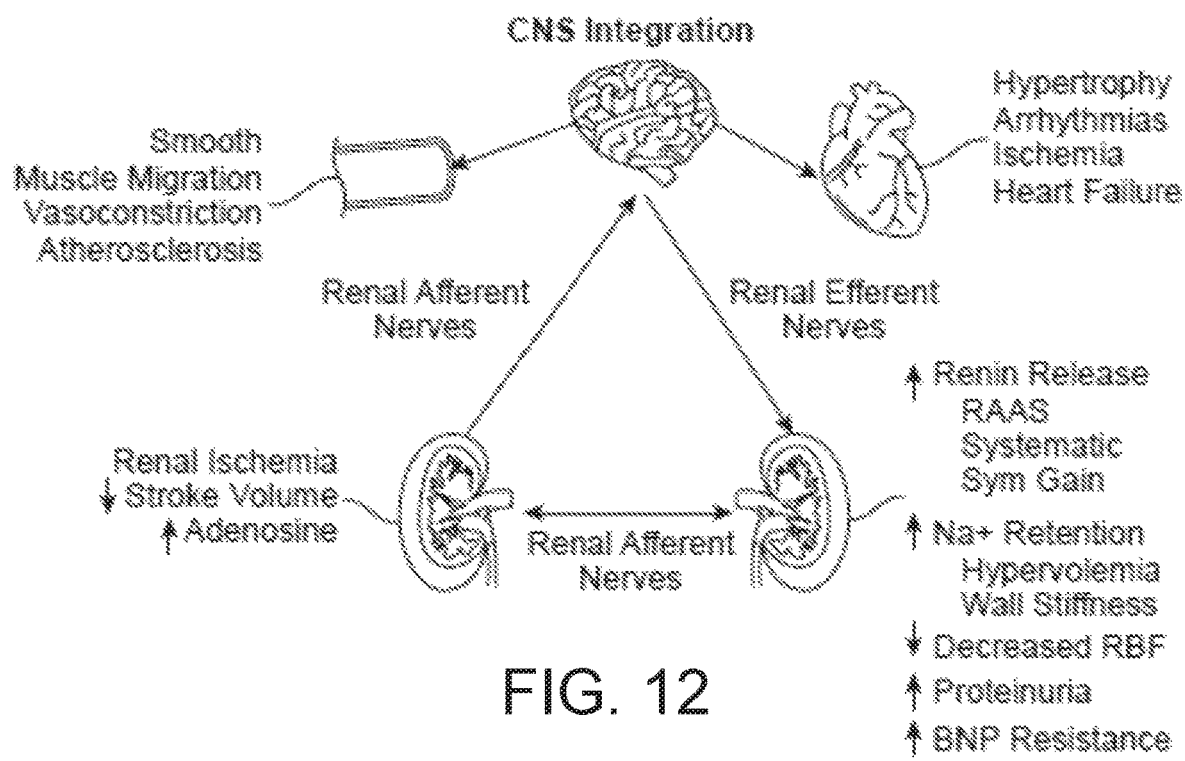

The kidneys communicate with integral structures in the central nervous system via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 11 and 12, this afferent communication might be from the kidney to the brain or might be from one kidney to the other kidney (via the central nervous system). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic over activity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, salt retention, and reduction of renal blood flow, and that (ii) modulation of tissue with afferent sensory nerves will reduce the systemic contribution to hypertension and other disease states associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

B. Additional Clinical Benefits of Renal Denervation

As provided above, renal denervation is likely to be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Since the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves, including those identified in FIG. 9. For example, as previously discussed, a reduction in central sympathetic drive may reduce the insulin resistance that afflicts people with metabolic syndrome and Type II diabetics. Additionally, patients with osteoporosis are also sympathetically activated and might also benefit from the down regulation of sympathetic drive that accompanies renal denervation.

C. Achieving Intravascular Access to the Renal Artery

Figure 13:
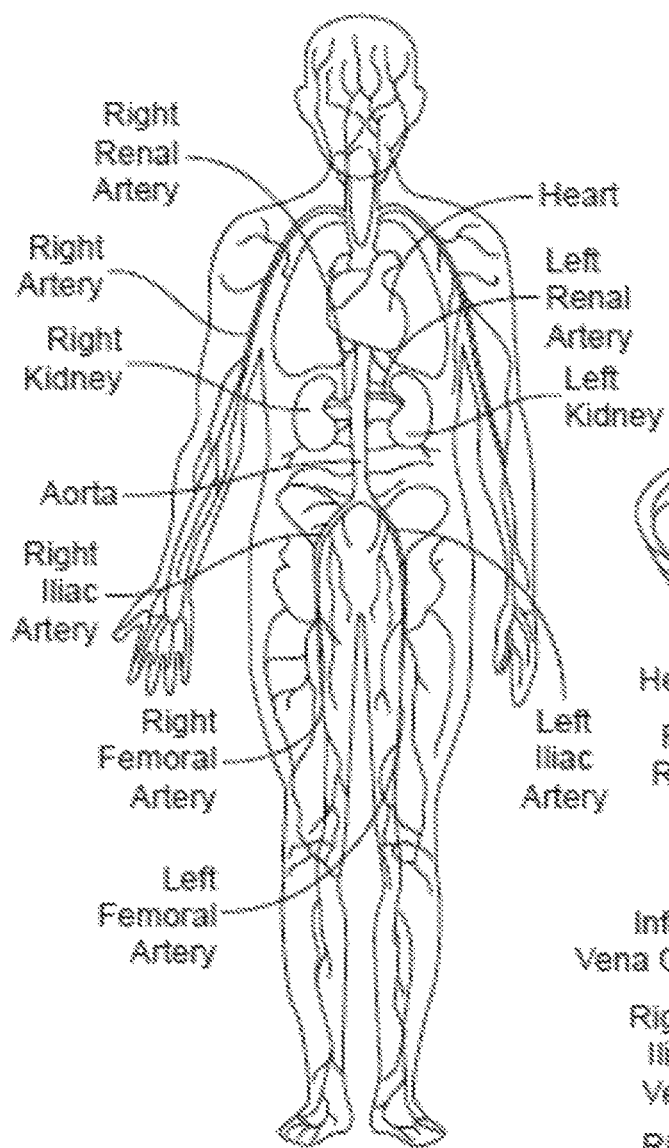
FIGS. 13 and 14 are anatomic views of the arterial vasculature and venous vasculature, respectively, of a human.

In accordance with the present technology, neuromodulation of a left and/or right renal plexus (RP), which is intimately associated with a left and/or right renal artery, may be achieved through intravascular access. As FIG. 13 shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

Figure 14:
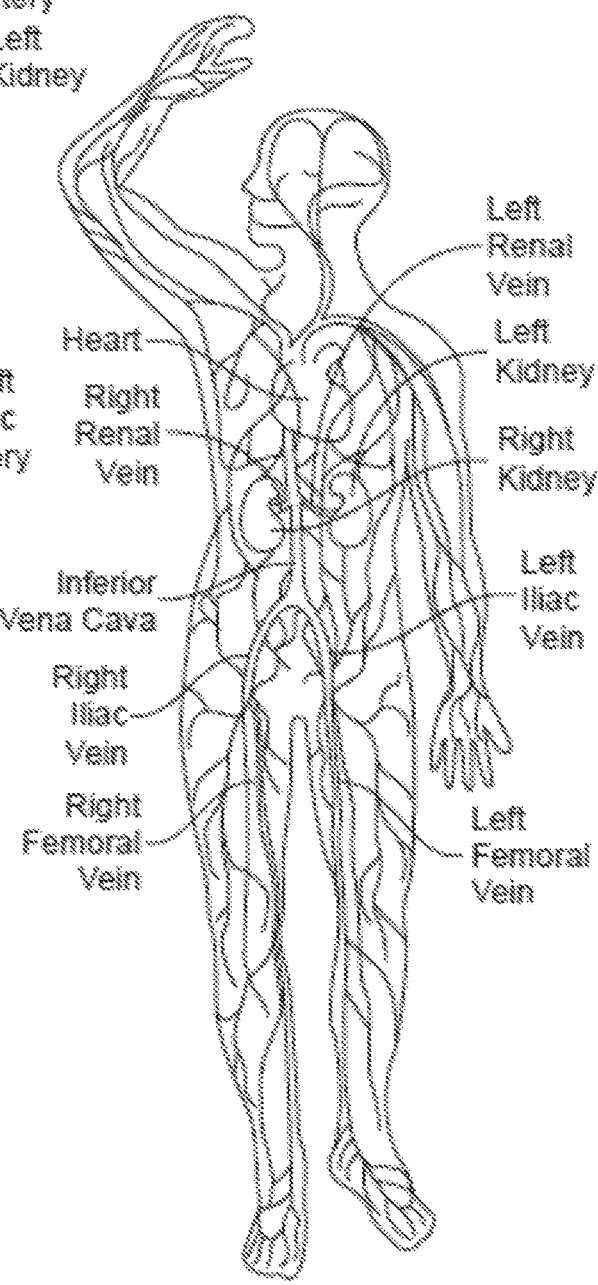

As FIG. 14 shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

D. Properties and Characteristics of the Renal Vasculature

Since neuromodulation of a left and/or right renal plexus (RP) may be achieved in accordance with the present technology through intravascular access, properties and characteristics of the renal vasculature may impose constraints upon and/or inform the design of apparatus, systems, and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/mechanical, spatial, fluid dynamic/hemodynamic and/or thermodynamic properties.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access should account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. For example, navigation can be impeded by the tight space within a renal artery, as well as tortuosity of the artery. Furthermore, establishing consistent contact is complicated by patient movement, respiration, and/or the cardiac cycle because these factors may cause significant movement of the renal artery relative to the aorta, and the cardiac cycle may transiently distend the renal artery (i.e. cause the wall of the artery to pulse).

Even after accessing a renal artery and facilitating stable contact between neuromodulatory apparatus and a luminal surface of the artery, nerves in and around the adventia of the artery should be safely modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient energy should be delivered to or heat removed from the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Given that this thrombus may cause a kidney infarct, thereby causing irreversible damage to the kidney, thermal treatment from within the renal artery should be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery.

The neuromodulatory apparatus should also be configured to allow for adjustable positioning and repositioning of the energy delivery element within the renal artery since location of treatment may also impact clinical efficacy. For example, it may be tempting to apply a full circumferential treatment from within the renal artery given that the renal nerves may be spaced circumferentially around a renal artery. In some situations, a full-circle lesion likely resulting from a continuous circumferential treatment may be potentially related to renal artery stenosis. Therefore, the formation of more complex lesions along a longitudinal dimension of the renal artery and/or repositioning of the neuromodulatory apparatus to multiple treatment locations may be desirable. It should be noted, however, that a benefit of creating a circumferential ablation may outweigh the potential of renal artery stenosis or the risk may be mitigated with certain embodiments or in certain patients and creating a circumferential ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging. Manipulation of a device in a renal artery should also consider mechanical injury imposed by the device on the renal artery. Motion of a device in an artery, for example by inserting, manipulating, negotiating bends and so forth, may contribute to dissection, perforation, denuding intima, or disrupting the interior elastic lamina.

Blood flow through a renal artery may be temporarily occluded for a short time with minimal or no complications. However, occlusion for a significant amount of time should be avoided because to prevent injury to the kidney such as ischemia. It could be beneficial to avoid occlusion all together or, if occlusion is beneficial to the embodiment, to limit the duration of occlusion, for example to 2-5 minutes.

Based on the above described challenges of (1) renal artery intervention, (2) consistent and stable placement of the treatment element against the vessel wall, (3) effective application of treatment across the vessel wall, (4) positioning and potentially repositioning the treatment apparatus to allow for multiple treatment locations, and (5) avoiding or limiting duration of blood flow occlusion, various independent and dependent properties of the renal vasculature that may be of interest include, for example, (a) vessel diameter, vessel length, intima-media thickness, coefficient of friction, and tortuosity; (b) distensibility, stiffness and modulus of elasticity of the vessel wall; (c) peak systolic, end-diastolic blood flow velocity, as well as the mean systolic-diastolic peak blood flow velocity, and mean/max volumetric blood flow rate; (d) specific heat capacity of blood and/or of the vessel wall, thermal conductivity of blood and/or of the vessel wall, and/or thermal convectivity of blood flow past a vessel wall treatment site and/or radiative heat transfer; (e) renal artery motion relative to the aorta induced by respiration, patient movement, and/or blood flow pulsatility; and (f) the take-off angle of a renal artery relative to the aorta. These properties will be discussed in greater detail with respect to the renal arteries. However, dependent on the apparatus, systems and methods utilized to achieve renal neuromodulation, such properties of the renal arteries, also may guide and/or constrain design characteristics.

As noted above, an apparatus positioned within a renal artery should conform to the geometry of the artery. Renal artery vessel diameter, $D_{RA}$, typically is in a range of about 2-10 mm, with most of the patient population having a $D_{RA}$ of about 4 mm to about 8 mm and an average of about 6 mm. Renal artery vessel length, $L_{RA}$, between its ostium at the aorta/renal artery juncture and its distal branchings, generally is in a range of about 5-70 mm, and a significant portion of the patient population is in a range of about 20-50 mm. Since the target renal plexus is embedded within the adventitia of the renal artery, the composite Intima-Media Thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment is important to reach the target neural fibers, the treatment should not be too deep (e.g., >5 mm from inner wall of the renal artery) to avoid non-target tissue and anatomical structures such as the renal vein.

An additional property of the renal artery that may be of interest is the degree of renal motion relative to the aorta induced by respiration and/or blood flow pulsatility. A patient's kidney, which is located at the distal end of the renal artery, may move as much as 4" cranially with respiratory excursion. This may impart significant motion to the renal artery connecting the aorta and the kidney, thereby requiring from the neuromodulatory apparatus a unique balance of stiffness and flexibility to maintain contact between the energy delivery element and the vessel wall during cycles of respiration. Furthermore, the take-off angle between the renal artery and the aorta may vary significantly between patients, and also may vary dynamically within a patient, e.g., due to kidney motion. The take-off angle generally may be in a range of about 30°-135°.

V. Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments. All references cited herein are incorporated by reference as if fully set forth herein.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Certain aspects of the present technology may take the form of computer-executable instructions, including routines executed by a controller or other data processor. In some embodiments, a controller or other data processor is specifically programmed, configured, and/or constructed to perform one or more of these computer-executable instructions. Furthermore, some aspects of the present technology may take the form of data (e.g., non-transitory data) stored or distributed on computer-readable media, including magnetic or optically readable and/or removable computer discs as well as media distributed electronically over networks. Accordingly, data structures and transmissions of data particular to aspects of the present technology are encompassed within the scope of the present technology. The present technology also encompasses methods of both programming computer-readable media to perform particular steps and executing the steps.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A system, comprising:
a neuromodulation catheter including:
an elongated shaft having a distal portion configured to be intravascularly positioned at a target site within a blood vessel of a human patient, and
a plurality of ablation electrodes spaced apart along the distal portion of the shaft, the plurality of ablation electrodes including a first ablation electrode and a second ablation electrode, wherein the ablation electrodes are configured to deliver neuromodulation energy to target nerves at or adjacent the target site;
a plurality of reference electrodes configured to be positioned at the patient's skin, the reference electrodes including a first reference electrode and a second reference electrode;
a controller configured to be communicatively coupled to the ablation electrodes and the references electrodes, wherein the controller is further configured to:
obtain a first impedance measurement between the first ablation electrode and the first reference electrode,
obtain a second impedance measurement between the first ablation electrode and the second reference electrode,
obtain a third impedance measurement between the second ablation electrode and the first reference electrode,
obtain a fourth impedance measurement between the second ablation electrode and the second reference electrode,
compare the first impedance measurement, the second impedance measurement, the third impedance measurement, and the fourth impedance measurement to at least one reference impedance value, and
based on comparison of the first impedance measurement, the second impedance measurement, the third impedance measurement, and the fourth impedance measurement to the at least one reference impedance value: (a) identify a first electrode group consisting of the first ablation electrode and one of the first reference electrode or the second reference electrode, and (b) identify a second electrode group consisting of the second ablation electrode and the other of the first reference electrode or the second reference electrode, wherein the first electrode group and the second electrode group are selected to achieve at least one of a desired direction or a desired three-dimensional shape of an electric field during subsequent energy delivery through at least one of the first electrode group or the second electrode group.

2. The system of claim 1 wherein the at least one reference impedance value comprises at least one of the first impedance measurement, the second impedance measurement, the third impedance measurement, or the fourth impedance measurement, and wherein the controller is configured to compare the first impedance measurement, the second impedance measurement, the third impedance measurement, and the fourth impedance measurement to the at least one reference impedance value by at least comparing at least one of the first, the second, the third, or the fourth impedance measurements to another of the first, the second, the third, and the fourth impedance measurements.

3. The system of claim 1 wherein the at least one reference impedance value comprises at least one of the first impedance measurement, the second impedance measurement, the third impedance measurement, or the fourth impedance measurement, and wherein the controller is configured to compare the first impedance measurement, the second impedance measurement, the third impedance measurement, and the fourth impedance measurement to the at least one reference impedance value by at least comparing each of the first, the second, the third, and the fourth impedance measurements to each of the other first, second, third, and fourth impedance measurements.

4. The system of claim 1 wherein the at least one reference impedance value comprises one or more stored impedance values, and wherein the controller is configured to compare the first impedance measurement, the second impedance measurement, the third impedance measurement, and the fourth impedance measurement to the at least one reference impedance value by at least comparing each of the first, the second, the third, and the fourth impedance measurements to the one or more stored impedance values.

5. The system of claim 1 wherein the controller is configured to generate an impedance map of the blood vessel at the target site based on the first, the second, the third, and the fourth impedance measurements.

6. The system of claim 1, further comprising an energy generator electrically coupled to the plurality of ablation electrodes, the plurality of reference electrodes, and the controller, and wherein, in response to the identification of the first electrode group and the second electrode group, the controller is configured to automatically cause the energy generator to: (a) deliver neuromodulation energy via a first electrical current through the first electrode group, and (b) deliver neuromodulation energy via a second electrical current through the second electrode group.

7. The system of claim 6 wherein the controller is an integral component of the energy generator and the controller and energy generator share a common housing.

8. The system of claim 1 wherein the controller is configured to indicate the first electrode group and the second electrode group to a user via a display.

9. The system of claim 1, further comprising an energy generator, wherein:
the controller is configured to obtain the first, the second, the third, and the fourth impedance measurements while the ablation electrodes are delivering neuromodulation energy, and
in response to the identification of the first electrode group and the second electrode group, the controller is configured to automatically cause the energy generator to—
(a) stop delivering neuromodulation energy via a first electrical current through (i) the first electrode and (ii) one of the plurality of reference electrodes that is not in the first electrode group, and
(b) start delivering neuromodulation energy via a second electrical current through the first electrode group.

10. The system of claim 1 wherein the distal portion of the shaft is configured to be positioned in at least one of a renal artery main vessel, a main bifurcation of the renal artery, or one or more renal branches distal of the main bifurcation of the renal artery.

11. The system of claim 1 wherein the distal portion of the shaft is configured to transform into a spiral shape such that, when the distal portion is placed in the spiral shape while positioned within the blood vessel, at least one of the ablation electrodes contacts an inner surface of a wall of the blood vessel.

12. The system of claim 1 wherein the number of reference electrodes is greater than the number of ablation electrodes.

13. A method, comprising:
positioning a plurality of reference electrodes at the skin of a human patient such that each of the reference electrodes is spaced apart from the other reference electrodes, wherein the reference electrodes include a first reference electrode and a second reference electrode;
intravascularly positioning a neuromodulation assembly within a blood vessel of the patient at a treatment site, the neuromodulation assembly a first ablation electrode and a second ablation electrode spaced apart from the first ablation electrode;
obtaining a first impedance measurement between the first ablation electrode and the first reference electrode;
obtaining a second impedance measurement between the first ablation electrode and the second reference electrode;
obtaining a third impedance measurement between the second ablation electrode and the first reference electrode;
obtaining a fourth impedance measurement between the second ablation electrode and the second reference electrode;
comparing the first impedance measurement, the second impedance measurement, the third impedance measurement, and the fourth impedance measurement to at least one reference impedance value; and
based on the comparison of the first impedance measurement, the second impedance measurement, the third impedance measurement, and the fourth impedance measurement to the at least one reference impedance value: (a) identifying a first electrode group consisting of the first ablation electrode and one of the first reference electrode or the second reference electrode, and (b) identifying a second electrode group consisting of the second ablation electrode and the other of the first reference electrode or the second reference electrode, wherein the first electrode group and the second electrode group are selected to achieve at least one of a desired direction or a desired three-dimensional shape of an electric field during subsequent energy delivery through at least one of the first electrode group or the second electrode group.

14. The method of claim 13, further comprising:
in response to identifying the first electrode group and the second electrode group, automatically delivering neuromodulation energy to the treatment site by delivering a first electrical current through the first electrode group and delivering a second electrical current through the second electrode group.

15. The method of claim 13 wherein positioning the plurality of reference electrodes includes positioning at least one of the plurality of reference electrodes at the patient's abdomen, at least one of the plurality of reference electrodes at the patient's torso, and at least one of the plurality of reference electrodes at one or both of the patient's legs.

16. The method of claim 13, wherein the at least one reference impedance value comprises at least one of the first impedance measurement, the second impedance measurement, the third impedance measurement, or the fourth impedance measurement, and wherein comparing the first impedance measurement, the second impedance measurement, the third impedance measurement, and the fourth impedance measurement to the at least one reference value comprises comparing at least one of the first, the second, the third, or the fourth impedance measurements to another of the first, the second, the third, and the fourth impedance measurements.

17. The method of claim 13, wherein the at least one reference impedance value comprises at least one of the first impedance measurement, the second impedance measurement, the third impedance measurement, or the fourth impedance measurement, and wherein comparing the first impedance measurement, the second impedance measurement, the third impedance measurement, and the fourth impedance measurement to the at least one reference value comprises comparing each of the first, the second, the third, and the fourth impedance measurements to each of the other first, second, third, and fourth impedance measurements.

18. The method of claim 13, wherein the at least one reference impedance value comprises one or more stored impedance values, and wherein comparing the first impedance measurement, the second impedance measurement, the third impedance measurement, and the fourth impedance measurement to the at least one reference value comprises further comprising comparing each of the first, the second, the third, and the fourth impedance measurements to the one or more stored impedance values.

19. The method of claim 13, further comprising generating an impedance map of the blood vessel at the target site based on the first, the second, the third, and the fourth impedance measurements.

20. The method of claim 13, further comprising indicating the first electrode group and the second electrode group to a user via a display.

21. The method of claim 13 wherein obtaining the first, the second, the third, and the fourth impedance measurements occur while the ablation electrodes are delivering neuromodulation energy.

22. The method of claim 13, further comprising:

in response to the identification of the first electrode group and the second electrode group, automatically causing an energy generator to: (a) stop delivering neuromodulation energy via a first electrical current through (i) the first electrode and (ii) one of the plurality of reference electrodes that is not in the first electrode group, and (b) start delivering neuromodulation energy via a second electrical current through the first electrode group.

23. The method of claim 13 wherein intravascularly positioning the neuromodulation assembly includes positioning the neuromodulation assembly in at least one of a renal artery main vessel, a main bifurcation of the renal artery, or one or more renal branches distal of the main bifurcation of the renal artery.

* * * * *